United States Patent [19]

Sportoletti

[11] 4,329,340
[45] May 11, 1982

[54] PHARMACEUTICAL COMPOSITION HAVING ANTIPHLOGISTIC, ANTIPYRETIC AND ANALGESIC ACTIVITY

[75] Inventor: Giancarlo Sportoletti, Milan, Italy
[73] Assignee: Italfarmaco S.p.A., Milan, Italy
[21] Appl. No.: 214,204
[22] Filed: Dec. 8, 1980

[30] Foreign Application Priority Data
Aug. 5, 1980 [IT] Italy ................................ 23998 A/80

[51] Int. Cl.³ ............................................ A61K 31/625
[52] U.S. Cl. .................................................... 424/232
[58] Field of Search ........................................ 424/232

*Primary Examiner*—Stanley J. Friedman
*Attorney, Agent, or Firm*—Bucknam and Archer

[57] ABSTRACT

Pharmaceutical compositions exhibiting antiphlogistic, antipyretic, analgesic activity and high gastroenteric tolerance are described. The active ingredient is imidazole salicylate of chemical formula (I).

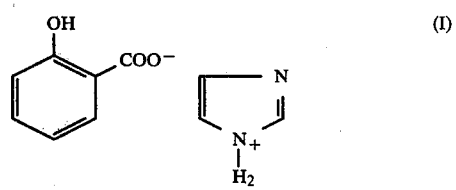

6 Claims, No Drawings

PHARMACEUTICAL COMPOSITION HAVING ANTIPHLOGISTIC, ANTIPYRETIC AND ANALGESIC ACTIVITY

The present invention relates to pharmaceutical compositions having antiphlogistic, antipyretic and analgesic activity. More specifically, the present invention relates to compositions having as the active component imidazole salicylate of chemical formula (I).

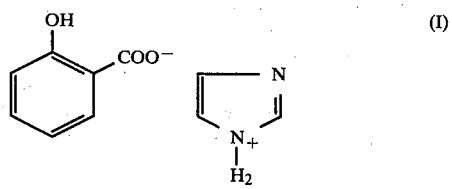

The compound of formula (I) is known in the art but the pharmacological activity has not been described. It has now been found surprisingly that the compound exhibits very significant antiphlogistic, antipyretic and analgesic activity.

Several pharmacological compositions containing derivatives of salicylic acid and exhibiting antiphlogistic activity are well known. These compositions have the disadvantages that, in animals as well as in humans, particularly on repeated administration, they cause gastroenteric lesions which obviously limit substantially their therapeutic use. This side effect appears to be connected with the mechanism of antiphlogistic activity.

It has now been found that imidazole salicylate of formula (I) exhibits the same activity described hereinabove without exhibiting the side effects of gastroenteric lesions. This constitutes a clear and substantial therapeutic improvement with respect to the known pharmaceutical compositions. In addition, the several pharmacotoxicological properties of the compound of formula (I) are more advantageous when compared to the properties of salicyclic acid and of imidazole when they are administered separately. More specifically, imidazole salicylate exhibits a greater antiphlogistic activity and a superior tolerability on a gastroenteric level when compared to salicylic acid and to salts of salicylic acids with inorganic cations.

The data reported hereinbelow demostrated that the properties of the compound of Formula (I) may be advantageously utilized for the preparation of pharmaceutical compositions which may be used by any route including the topical route.

METHOD OF PREPARATION

Salicylic acid, one mole (138.128 grams), and one mole of imidazole (68.088 grams) are dissolved in 700 cc of analytically pure methanol. The mixture is allowed to stand overnight. The solution is then evaporated at atmospheric pressure to a volume of 200 cc at which point, under stirring, the material crystallizes. The solution is redissolved in about 300 cc of boiling methanol and the solution is evaporated to a volume of about 250 cc. After crystallization has begun, diethyl ether in the amount of 50 cc, is added and the mixture is allowed to stand at a temperature of $-20°$ C. The solid which is formed is filtered off and washed with a small amount of cold methanol and ether.

The material obtained amounts to 150 grams of wet product. The product is recrystallized from a mixture of methanol and ether, thus obtaining 110 grams of material. An additional amount of 69 grams of crystalline material is obtained from the mother liquor by evaporation and crystallization from methanol and ether.

Analytical data:
Melting point: 123–124° C.
Elementary analysis:

| Theory (%): | Found (%): |
|---|---|
| C:58.25 | 57.90 |
| H:4.89 | 4.98 |
| N:13.58 | 13.80. |
| Ultraviolet absorption spectrum: | $\lambda_{max} = 300$nm; |
| $E^{1\%}_{1cm} = 182.5$ | |
| Water solubility >100 mg/cc | |

The infrared spectrum of the substance confirms the structure hereinbelow:

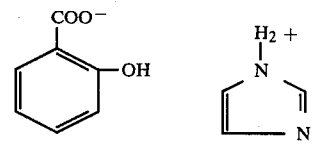

PHARMACO-TOXICOLOGICAL PROPERTIES (a) Acute Toxicity

Imidazole salicylate is referred to hereinbelow with the symbol SZ. The $DL_{50}$ in mice after a single administration by the oral route in animals of both sexes is 1109 mg/kg of body weight. The $DL_{50}$ of sodium salicylate is 1600 mg/kg. and in the case of imidazole it is 880 mg/kg. Therefore, the acute toxicity of SZ is intermediate between the value of sodium salicylate and imidazole and it is closer to the $DL_{50}$ of acetylsalicylic acid.

On the basis of literature reports, (Arrigoni Martelli E., Aspects of the Pharmacology of Inflammation. Tamburini Ed. (1973, p. 127) the $DL_{50}$ of acetylsalicylic acid administered orally in the same species is 1050 mg/kg of body weight.

The $DL_{50}$ determined experimentally for imidazole is very close to the value reported by Puig Muset P. et al, Biochemical and Pharmacological Aspects of Imidazole, P.E.V.Y.F., Barcellona 1972 which is 885 mg/kg of body weight.

(b) Sub-acute Toxicity

The sub-acute toxicity has been tested in Wistar rats during the growth phase by daily administration of doses of 50, 100 and 200 mg/kg, by administering every day of the week to groups of ten (10) animals the substance by the gastric tube.

The following parameters are studied: the behavior, the body weight, the most important biochemical and clinical values and at the end of the test the macro- and microscopic condition of the animals. In each group the growth has occurred normally and biochemical and morphological changes have not been noted. In some animals of each group treated with the highest dosage a decrease of the strength required for grasping objects has been noted.

It should be stressed, particularly, that lesions in the nature of ulcers and hemorrhage at the level of the digestive mucosa have not been seen.

It is proper, therefore, to conclude that dosages in the range of 1/10 of the $DL_{50}$ are not toxic on repeated administration.

(c) Analgesic Activity

Analgesic activity has been demonstrated according to the test of Writhing with phenylquinone in mus muscle according to the method of Siegmund E. et al, Proc. Soc. Experimental Biol. Med., 95, 729, 1957, with doses of SZ between 50 and 300 mg/kg/os. One dose of SZ of 206 mg/kg orally has resulted in 46% inhibition of the response and the equimolar dose of imidazole has not demonstrated any activity.

With this test the activity of SZ is lower than the activity of acetylsalicylic acid which under the same experimental conditions has given the following results:
50 mg/kg/os inhibition: 52%
100 mg/kg/os inhibition: 94%
indomethacin 5 mg/kg/os
inhibition: 92%

On the basis of literature data the $DE_{50}$ of acetylsalicylic acid varies in the Writhing test as a function of the irritating agent between 18 and 90 mg/kg/os and the $DE_{50}$ of imidazole varies between 23 and 120 mg/kg/os according to the report of Puig—Parellada P., et al, Pharmacology 10, 161, 1973.

(d) Antiphlogistic Activity

The antiphlogistic activity of SZ has been demonstrated with the carrageenin test in rats according to the procedure of Winter C. A., Proc. Soc. Exp. Biol. III, 544, 1962 and in the granuloma from cotton pellets in rats according to Winter, C. A. et al., J. Pharmacol. exper. ther. 141, 369, 1963.

The activity is demonstrated to be in a dosage of between 50 and 200 mg/kg/os.

In the edema resulting from carrageenin which is the test in which the substance exhibits the greatest activity, the $DE_{50}$ is 150 mg/kg/os (L.F. 50-200). On the other hand, imidazole in a dosage between 33-99 mg/kg/os is inactive and sodium salicylate has a $DE_{50}$ of about 240 mg/kg/os. With this test acetylsalicylic acid tested by us in a dose of 50-200 mg/kg/os has given inhibition of 50-80%.

The antiphlogistic activity of the substance results, therefore, in the range of the activity of acetylsalicylic acid and is superior to the activity of sodium salicylate.

(e) Antipyretic Activity

The antipyretic activity of SZ has been demonstrated with the test of hyperthermia caused by Brewer's Yeast according to Eagle J., Pharmacol. Exper. Ther. 99, 450, 1950 in rats. This activity results to be the greatest, that is, gives complete protection against fever in the dosage of 100 mg/kg/os. Superior doses, that is, 200-300 mg/kg/os give slight hyperthermia.

With this test, acetylsalicyclic acid has exhibited an activity equivalent to the dose of 200 mg/kg/os. Imidazole in the dosage of 68 mg, which is equivalent to 206 mg of SZ, has resulted inactive. On the basis of literature reports (Puig Parellado, loc. cit.) it is clear that imidazole exhibits antihyperthermic activity in the dosage of 200 mg/kg/os and higher.

The substance SZ, therefore, exhibits antipyretic activity superior to acetylsalicylic acid.

(f) Specificity of Antithermic, Antiphlogistic and Analgesic Activity

The compound SZ in the dosage required to exert antithermic, antiphlogistic and analgesic activity has no effect on the behavior, motor function and vegetative functions of the animal tested. Only in the dosage of 200 mg/kg/os one notes an increase in the spontaneous motility.

(b) Ulcerogenic Activity

In the course of sub-acute treatment with doses of 50-100-200 mg/kg/os daily repeated for a period of five weeks in rats fed normally, symptoms of ulcerative gastritis with hemorrhage have not been noted, and symptoms of gastro-duodenal ulcers have not been noted.

With the test of causing ulcerative gastritis accompanied by hemorrhage caused by prolonged fasting (4 gg at ambient temperature) in the last period of sub-acute treatment carried out for a total of seventeen (17) days with 200 mg/kg/os, the ulcerogenic activity of the substance SZ (estimated as increments of the gravity of the ulcerogenic situation of the non-treated controls has resulted to be substantially lower than that obtained from an equimolar dose of sodium salicylate or aspirin, as far as the number of ulcers in a stomach, the total number of ulcers and the number of bleeding ulcers.

(h) Activity on Biosynthesis of Prostaglandin

The activity of the substance SZ has been studied in comparison with sodium salicylate, imidazole and indomethacin according to the method of Vane Y. R., Nature New Biol. 231, 239, 1971.

A typical experiment shows that sodium salicylate in the concentration of 100 $\mu g/ml$ inhibits completion of the biosynthesis of both PG E as well as PG F. Indomethacin in the concentration of 1 $\mu g/ml$ gives an inhibition of 30-40%. Imidazole in the concentration of 100 $\mu g/ml$ stimulates the biosynthesis of PG E without affecting the synthesis of PG F. The substance SZ in the concentration of 100 $\mu g/ml$ dose not affect the synthesis of PG E nor the synthesis of PG F.

(i) Tests on Genetic Mutation

In several tests for genetic mutation, the substance SZ has not exhibited any mutagenic activity with or without metabolic activation.

In conclusion, the substance SZ exhibits a specific antipyretic and antiphlogistic activity which is equivalent to the activity of acetylsalicylic acid, but the ulcerogenic activity is substantially lower and the inhibitory action with respect to the biosynthesis of prostaglandin is substantially lower.

The substance may be administered in the form of tablets, capsules, pills, in solutions or suspension, with inert carriers.

A suitable dose is:
(1) (tablets or drops):
   (a) children: 4-8 mg/kg, 1-4 times a day;
   (b) adults: 250-600 mg, 1-4 times a day;
(2) intravenously:
   adults: 500 mg, 1-2 times a day;
(3) intramuscular injection:
   (a) children: 100 mg, 1-2 times a day;
   (b) adults: 300 mg, 1-4 times a day;
(4) suppositories:
   (a) children: 250 mg, 1-2 times a day;
   (b) adults: 500 mg, 1-2 times a day;
(5) topically:
   cream with 5-10-20% of active principle.

What is claimed is:

1. The method of relieving a living subject affected by inflammation, which consists of administering to said subject a composition containing imidazole salicylate as the active ingredient in the amount of 100-600 mgs per unit dose 1-4 times a day.

2. The method of relieving a living subject affected by high fever, which consists of administering to said subject a composition containing imidazole salicylate as the active ingredient in the amount of 100–600 mgs per unit dose 1–4 times a day.

3. The method of relieving a living subject affected by pain, which consists of administering to said subject a composition containing imidazole salicylate as the active ingredient in the amount of 100–600 mgs per unit dose 1–4 times a day.

4. A pharmaceutical composition exhibiting antiphlogistic, antipyretic, analgesic activity and high gastroenteric tolerance in unit dosage form in the form of tablets, capsules, pills suitable for oral administration which contains as the active ingredient imidazole salicylate in the amount of 250–600 mgs and an inert carrier.

5. A pharmaceutical composition in unit dosage form in the form of suppositories containing 250–500 mgs of imidazole salicylate and inert carriers.

6. A pharmaceutical composition in the form of a cream suitable for administration by topical application which contains 5–20% of said imidazole salicylate and an inert carrier.

* * * * *